(12) United States Patent
Law et al.

(10) Patent No.: US 9,010,584 B2
(45) Date of Patent: Apr. 21, 2015

(54) DISPENSERS

(71) Applicant: Rieke Corporation, Auburn, IN (US)

(72) Inventors: Brian Robert Law, Leicester (GB); David John Pritchett, Ashby de la Zouch (GB); Roy Cox, Alderton (GB)

(73) Assignee: Rieke Corporation, Auburn, IN (US)

( * ) Notice: Subject to any disclaimer, the term of this patent is extended or adjusted under 35 U.S.C. 154(b) by 0 days.

(21) Appl. No.: 13/727,885

(22) Filed: Dec. 27, 2012

(65) Prior Publication Data

US 2013/0112716 A1    May 9, 2013

Related U.S. Application Data

(63) Continuation of application No. PCT/GB2011/001002, filed on Jul. 1, 2011.

(30) Foreign Application Priority Data

Jul. 1, 2010    (GB) .................................. 1011143.3

(51) Int. Cl.
   *G01F 11/00*    (2006.01)
   *B65D 5/72*    (2006.01)
   (Continued)

(52) U.S. Cl.
   CPC ............ *B05B 11/0027* (2013.01); *A61M 11/00* (2013.01); *B05B 11/0005* (2013.01);
   (Continued)

(58) Field of Classification Search
   USPC ........... 222/256, 259, 321.7, 321.9, 387, 494, 222/491, 496, 495, 571, 258, 257, 511, 222/321.1, 321.8, 501, 322, 153.13; 141/114; 604/275, 278, 245, 249, 68, 604/69, 70
   See application file for complete search history.

(56) References Cited

U.S. PATENT DOCUMENTS 1,283,050 A * 10/1918 Berg .............................. 222/322
2,774,517 A    12/1956 Teegardin et al.
(Continued)

FOREIGN PATENT DOCUMENTS

DE    39 29 064 A    1/1991
EP    0 098 939 A2    1/1984
(Continued)

OTHER PUBLICATIONS

European Patent Application 04255318 Search Report mailed Jun. 14, 2006.
(Continued)

*Primary Examiner* — Kevin P Shaver
*Assistant Examiner* — Stephanie E Williams
(74) *Attorney, Agent, or Firm* — Woodard Emhardt Moriarty McNett & Henry LLP

(57) ABSTRACT

A pump dispenser is intended for oral administration of medicines. A pump receives fluid product through a valved inlet from a container, preferably of the airless type with a follower piston. The dispenser may be a movable-nozzle or fixed-nozzle dispenser. The discharge outlet of the dispenser has a stub nozzle incorporating a closure valve. A spring urges the closure valve forward to close a discharge opening of the stub nozzle. The nozzle attachment is shaped for oral dosing and has an internal rearwardly-projecting actuating structure which, when the nozzle attachment is coupled onto the stub nozzle, pushes the closure valve open. When the nozzle attachment is removed the spring closes the outlet again. Child-resistant features are described for fitting the nozzle attachment to the stub nozzle.

32 Claims, 9 Drawing Sheets

(51) Int. Cl.
  *B65D 88/54* (2006.01)
  *A61M 31/00* (2006.01)
  *A61M 5/00* (2006.01)
  *A61M 5/30* (2006.01)
  *B05B 11/00* (2006.01)
  *A61M 11/00* (2006.01)

(52) U.S. Cl.
  CPC ......... *B05B11/0048* (2013.01); *B05B 11/0072* (2013.01); *B05B 11/0075* (2013.01); *B05B 11/3047* (2013.01); *B05B 11/3069* (2013.01); *B05B 11/3074* (2013.01); *B05B 11/3005* (2013.01); *B05B 11/3015* (2013.01); *B05B 11/3001* (2013.01)

(56) References Cited

U.S. PATENT DOCUMENTS

| | | |
|---|---|---|
| 2,919,056 A | 12/1959 | Collins |
| 3,379,136 A | 4/1968 | Corsette |
| 4,118,152 A | 10/1978 | Bron |
| 4,277,001 A | 7/1981 | Nozawa |
| 4,286,736 A | 9/1981 | Corsette et al. |
| 4,343,417 A | 8/1982 | Corsette |
| 4,360,130 A | 11/1982 | Nishimura et al. |
| 4,364,718 A | 12/1982 | Beun et al. |
| 4,371,098 A | 2/1983 | Nozawa et al. |
| 4,376,495 A * | 3/1983 | Spatz ............................. 222/46 |
| 4,496,082 A | 1/1985 | Corsette |
| 4,511,065 A | 4/1985 | Corsette |
| 4,515,298 A * | 5/1985 | Czech ........................... 222/380 |
| 4,589,573 A | 5/1986 | Tada |
| 4,673,109 A | 6/1987 | Cassia |
| 4,775,079 A | 10/1988 | Grothoff |
| 4,776,498 A | 10/1988 | Maerte et al. |
| 4,811,871 A | 3/1989 | Wass et al. |
| 4,856,679 A | 8/1989 | Czech |
| 4,872,596 A | 10/1989 | Corsette |
| 4,890,773 A * | 1/1990 | Corsette ........................ 222/380 |
| 4,958,752 A | 9/1990 | Maerte et al. |
| 5,016,780 A | 5/1991 | Moretti |
| 5,115,980 A | 5/1992 | SKorka |
| 5,165,577 A | 11/1992 | Ophardt |
| 5,282,552 A | 2/1994 | Ophardt |
| 5,353,969 A | 10/1994 | Balderrama |
| 5,373,970 A | 12/1994 | Ophardt |
| 5,401,148 A | 3/1995 | Foster et al. |
| 5,431,309 A | 7/1995 | Ophardt |
| 5,445,288 A | 8/1995 | Banks |
| 5,489,044 A | 2/1996 | Ophardt |
| 5,548,943 A | 8/1996 | Behar et al. |
| 5,676,277 A | 10/1997 | Ophardt |
| 5,738,250 A | 4/1998 | Gillingham et al. |
| 5,813,576 A | 9/1998 | Iizuka et al. |
| 5,904,272 A | 5/1999 | Kaufman et al. |
| 5,975,360 A | 11/1999 | Ophardt |
| 5,988,456 A | 11/1999 | Laible |
| 6,045,008 A | 4/2000 | Gonzalez et al. |
| 6,053,368 A * | 4/2000 | Geimer .................... 222/189.09 |
| 6,062,433 A | 5/2000 | Fuchs |
| 6,082,586 A | 7/2000 | Banks |
| 6,126,042 A | 10/2000 | Meshberg |
| 6,179,164 B1 | 1/2001 | Fuchs |
| 6,240,979 B1 | 6/2001 | Lorscheidt |
| 6,257,454 B1 | 7/2001 | Ritsche |
| 6,343,724 B1 | 2/2002 | Ophardt et al. |
| 6,409,050 B1 | 6/2002 | Ophardt et al. |
| 6,516,976 B2 | 2/2003 | Lewis et al. |
| 6,533,145 B2 | 3/2003 | Lewis et al. |
| 6,540,117 B2 | 4/2003 | Powling |
| 6,540,157 B2 | 4/2003 | Ophardt |
| 6,543,651 B2 | 4/2003 | Lewis et al. |
| 6,557,736 B1 | 5/2003 | Ophardt |
| 6,575,334 B2 | 6/2003 | Lewis et al. |
| 6,575,335 B2 | 6/2003 | Lewis et al. |
| 6,601,736 B2 | 8/2003 | Ophardt et al. |
| 7,004,356 B1 | 2/2006 | Sayers |
| 7,011,237 B1 | 3/2006 | Sayers et al. |
| 7,104,426 B2 | 9/2006 | Suzuki |
| 7,325,704 B2 | 2/2008 | Kasting |
| 7,367,476 B2 | 5/2008 | Law et al. |
| 7,461,762 B2 | 12/2008 | Law et al. |
| 7,654,418 B2 | 2/2010 | Law et al. |
| 7,690,535 B2 | 4/2010 | Law et al. |
| 7,891,522 B2 | 2/2011 | Law et al. |
| 8,118,193 B2 * | 2/2012 | Law ............................. 222/205 |
| 8,556,130 B2 * | 10/2013 | Law et al. ..................... 222/256 |
| 2002/0027144 A1 | 3/2002 | Lacout |
| 2003/0132252 A1 | 7/2003 | Rossignol |
| 2003/0201286 A1 | 10/2003 | Ophardt |
| 2004/0129733 A1 * | 7/2004 | Schultz ...................... 222/321.7 |
| 2004/0217137 A1 | 11/2004 | Ophardt |
| 2005/0051579 A1 | 3/2005 | Kasting |
| 2006/0043117 A1 | 3/2006 | Law et al. |
| 2007/0200010 A1 | 8/2007 | Girerd |
| 2007/0215643 A1 | 9/2007 | Law et al. |
| 2008/0197149 A1 | 8/2008 | Law et al. |
| 2008/0308183 A1 | 12/2008 | Law |
| 2009/0212074 A1 | 8/2009 | Brouwer |
| 2009/0218008 A1 * | 9/2009 | Law ......................... 141/311 R |
| 2010/0276515 A1 | 11/2010 | Milanese |
| 2012/0097714 A1 | 4/2012 | Hoefte et al. |

FOREIGN PATENT DOCUMENTS

| | | |
|---|---|---|
| EP | 0 274 256 A1 | 7/1988 |
| EP | 0 327 421 A1 | 8/1989 |
| EP | 0 389 688 A2 | 10/1990 |
| EP | 0 509 863 A1 | 10/1992 |
| EP | 0 600 286 A2 | 6/1994 |
| EP | 0 703 831 B1 | 12/1998 |
| EP | 1 092 447 A2 | 4/2001 |
| EP | 1 190 775 A1 | 3/2002 |
| EP | 1 015 341 B1 | 1/2004 |
| EP | 1 449 595 A1 | 8/2004 |
| EP | 1 514 607 A2 | 3/2005 |
| EP | 1 629 900 A2 | 3/2006 |
| EP | 1 671 705 A1 | 6/2006 |
| EP | 1 676 640 A1 | 7/2006 |
| EP | 2 095 882 A1 | 9/2009 |
| EP | 2 133 153 A1 | 12/2009 |
| EP | 2 153 908 A1 | 2/2010 |
| EP | 2 353 727 | 8/2011 |
| GB | 1149805 | 4/1969 |
| GB | 2360273 | 9/2001 |
| GB | 2360273 A | 9/2001 |
| JP | H08-011921 A | 1/1996 |
| WO | 99/49769 A1 | 10/1999 |
| WO | 03/101620 A1 | 12/2003 |
| WO | WO 2005/049477 A2 | 6/2005 |
| WO | WO 2010/023462 A1 | 4/2010 |

OTHER PUBLICATIONS

European Patent Application 05256914.2 Extended Search Report mailed Mar. 2, 2006.
European Search Report in corresponding EP 11250032.7 dated May 20, 2011.
Hygiene-Technik Inc., A member of the Ophardt Group of Companies, UX10 Lotion or Foam Soap Dispenser, 2004, pp. 2.
PCT/GB2011/001001 Search Report and Written Opinion dated Nov. 24, 2011.
PCT/GB2011/001002 Search Report and Written Opinion dated Sep. 26, 2011.
Pictures of Umbrella Valve from RD Industries of Omaha, Nebraska (Pictures 1-6), Jan. 4, 2005.
United Kingdom Patent Application 1100129.4 Search Report mailed Mar. 23, 2011.
PCT/IB2013/050101 International Preliminary Report on Patentability dated Jul. 8, 2014.
U.S. Appl. No. 12/685,064 to David John Pritchett, Office Action mailed Aug. 17, 2012.

* cited by examiner

DISPENSERS

CROSS-REFERENCE TO RELATED APPLICATIONS

This application is a continuation of International Application No. PCT/GB2011/001002 filed Jul. 1, 2011, which claims the foreign priority benefit of United Kingdom Application No. GB1011143.3 filed Jul. 1, 2010, both which are hereby incorporated by reference.

BACKGROUND

This invention has to do with dispensers for fluid products. The ideas described here have particular application in dispensers to be used for oral dosing of medicines, especially to children, but they may have other uses.

Conventionally, liquid oral medicines are administered with small spoons typically holding 5 ml. The medicine is poured from a bottle into the spoon. Where smaller doses are needed, e.g. for children, the spoon may be part-filled, or a smaller spoon used. It is not easy to pour a small dose accurately from a bottle. An alternative method is dosing by squirting into the mouth from a syringe. It is then easy to charge the accurate amount, but syringes are difficult to fill unless the container is specially adapted, and much more difficult than spoons to clean and dry.

Special problems arise when dosing very young children and babies, who may be unable to swallow the intended dose in one go. It is no use dispensing a dose accurately if the child chokes or spits part of it out.

It may be considered to use a pump dispenser in which, by a predetermined stroke of a piston-cylinder pump chamber mounted on a product container, a uniform volume can be dosed from the container to an outlet nozzle. Such dispensers are known for dosing animals. If a child could be dosed directly from the nozzle, a convenient way of providing fast, predetermined doses without a separate spoon would be available.

However pump dispensers in general have drawbacks in respect of this use. Fluid residues remain in the outlet nozzle after each stroke. These may dry out or become contaminated. In practice, pump outlet nozzles cannot be adequately hygienic even if a cover cap is provided. Moreover pump mechanisms are valved for forward flow. If a child sucked on the nozzle they might receive an excessive dose.

Here we put forward new ideas for dispenser outlets which address various issues discussed above.

SUMMARY

The disclosed embodiments relate in general to dispensers for fluid products, preferably a pump dispenser, having a discharge outlet with an outlet opening. The dispenser is operable to dispense a fluid product from a supply container in doses from the discharge outlet. In a pump dispenser, the typical dosing action is reciprocation of a pump plunger, which alters the volume of a pump chamber connected via an inlet to the supply container and via a discharge channel to the outlet opening. Usually the pump chamber is defined between a piston and cylinder, one of these (usually the piston) moving with the plunger. Pump chambers with deformable walls may also be used. Pump dispensers of the moveable-nozzle type, in which the discharge channel and outlet opening are comprised in the plunger, and of the fixed-nozzle type in which the discharge channel and outlet opening are part of or fixed relative to the pump body, are both possibilities. For dosing of oral compositions such as medicines a fixed-nozzle dispenser has advantages because the outlet can more easily be held steady.

As disclosed, the dispenser discharge outlet has an outlet closure valve with a closure mechanism comprising a closure member which in a closed position closes the discharge outlet. The dispenser also comprises a separate outlet attachment which defines an outlet conduit having a nozzle opening. The outlet attachment can be coupled to the dispenser at the outlet opening, by means of suitable coupling structure. Typically this comprises respective interfitting formations or coupling elements of the outlet attachment and of the dispenser adjacent to the outlet opening.

The outlet attachment comprises an actuating portion which, in the coupled condition, engages the closure mechanism of the dispenser to hold the closure valve in an open condition. In this open condition the dispenser discharge outlet is in fluid communication with the outlet conduit and nozzle opening of the outlet attachment, so that fluid product can be dispensed from the dispenser through its own outlet opening and thence through the outlet attachment.

When the outlet attachment is uncoupled from the dispenser—moved to an uncoupled condition or position—the closure mechanism is operable to move to a closed condition in which the closure member of its closure valve closes the outlet opening. Preferably the closure member is biased e.g. by a spring so that the closure mechanism automatically closes the dispenser outlet opening when the outlet attachment is uncoupled and removed.

The preferred embodiment of the closure mechanism is mechanically operated and not responsive to forward fluid pressure in the dispenser to open it. Indeed it may be arranged so that forward fluid pressure tends to keep it closed.

Preferably the actuating portion of the outlet attachment acts to drive the closure valve closure member back, i.e. in an upstream direction, out of its closed position. The actuating portion may act directly on the closure member, usually by direct contact, e.g. on a portion thereof exposed at the dispenser outlet opening. As mentioned, this may be against a forward or outward spring bias of the closure member so that when the outlet attachment is removed, or in general moved to a disengaged, uncoupled or non-actuated condition or position relative to the dispenser outlet, the closure member pushes out to re-close the outlet opening.

Preferably the closure member in the closed position is at the outlet opening. It may occupy the outlet opening at least substantially flush with, or projecting out beyond, a surround surface of the outlet opening so that after removal or disengagement of the outlet attachment, any residual fluid product is either enclosed in the dispenser behind the closure member—and so protected against drying out, contamination of the like—or is on the exterior of the dispenser so that it can be easily wiped or washed away, or else is in or on the separate outlet attachment which, being a removal tubular component separate from the dispenser, can easily be cleaned or replaced.

The dispenser outlet opening may be in a projecting nozzle, outlet stub or spigot of the dispenser, onto, over or into which the outlet attachment fixes. Alternatively the outlet opening could be in a flush face of the dispenser, or even recessed, although (depending on the mechanism and disposition of the closure member) this latter might make cleaning and/or securing of the outlet attachment more difficult.

The outlet attachment, which may also be considered as a discrete or removable extension tube or hygienic mouth adaptor for the dispenser outlet, is preferably a generally tubular component with a socket or plug portion shaped to fit conformingly onto or into a corresponding stub outlet, spigot or socket of the dispenser. Preferably this part of the dispenser also defines the outlet opening. The actuating portion of the outlet attachment may be provided in the tube thereof, e.g. moulded in one piece with the tube. It may be a rearwardly-directed formation e.g. projection positioned generally in the middle of the tube opening. A suitable mounting of the actuating portion is by means of one or more support elements or spokes connecting to an adjacent wall of the tube. When the outlet attachment is moved or put into the actuating or docked position on the stub outlet or spigot of the dispenser, the rearwardly-projecting actuating portion pushes the closure member of the dispenser closure mechanism back out of its blocking relation with the outlet opening, preferably against spring bias, to an open position.

The actuating portion of the outlet attachment is of course shaped and dimensioned so that it does not itself block the outlet opening. It will be understood that a similar effect could be achieved by having a forward non-blocking projection of the closure member, which can be engaged and pushed back by the actuating portion of the outlet attachment which may then not need to enter the dispenser outlet opening. This is less preferred because a part projecting from the outlet opening may be liable to damage.

Considering the closure mechanism, the closure member may be in the form of a front (outer) plug cooperating with a rear (inner) spring, deformed against its resilience, e.g. compressively, when the plug is pushed backwards. A compression spring may engage a rear abutment in the outlet structure. Any kind of spring may be used, but a preferred embodiment has one or more flexible rearward legs which bend against their resilience as the closure member is moved to the open position. A rear end of the or each leg may engage beside or around a central flow opening of the outlet structure, upstream of the eventual outlet opening. The closure member may be formed integrally with the spring or one or more elements thereof.

To facilitate assembly of the closure mechanism, preferably a discrete nozzle stub or spigot component defining the discharge outlet is fixed onto a body of the dispenser, defining between them a closure mechanism cavity for the closure mechanism or part thereof, e.g. a spring.

For guiding the closure plug, it may be slidable in a guide portion of the discharge channel immediately upstream of the outlet opening, having guide portions to contact the plug separated by flow clearances so that liquid can pass forward around the plug until it reaches its foremost, closed position.

The outlet attachment may secure to the dispenser body by any suitable coupling structure or retaining mechanism, e.g. a thread, push fit, interference fit, locking cams, bayonet-type fitting, wedge or taper fit etc. The coupling needs to retain the outlet attachment sufficiently positively to keep it in place and to keep the closure mechanism open.

The dispenser body portion to which the outlet attachment fits may be on the plunger of a moveable nozzle dispenser, or on a fixed part of a fixed-nozzle dispenser.

The outlet attachment may be shaped at its nozzle opening for suitability for oral dosing, i.e. to be put in the mouth. Desirably it has a surround surface tapering towards the nozzle opening, and which is smoothly curved or rounded i.e. without angles, edges or corners at this part. It may have circular symmetry around the nozzle axis. Or, it may have a flattened or beak-like outer form. In the latter case the coupling or retaining mechanism which holds the outlet attachment on the dispenser may then be alignment-selective, e.g. to provide only one or two possible coupled alignments of the nozzle attachment relative to the dispenser.

The dispenser may have a forwardly-acting outlet valve positioned upstream of the closure mechanism, e.g. an outlet valve of known or conventional type, for assuring re-filling of the pump chamber on a plunger recovery stroke.

Preferably the dispenser is of the "airless" type in which the product is dispensed from a container with a follower piston or from a collapsible container (or container liner) so that the container space remains essentially full of product.

One or more of the characteristic outlet attachments (separate nozzles) may be provided with the dispenser. More than one differently-sized or shaped nozzle attachment may be provided for use with a single dispenser, e.g. for dosing different sizes/ages of children. The dispenser may have an outer cover cap to cover the outlet structure. It may be arranged that the cover cap will not fit over the outlet structure with the outlet attachment in the coupled or actuated position. This encourages detachment or uncoupling of the nozzle after use, improving security.

Additionally or alternatively the coupling structure may provide for a preliminary holding engagement of the nozzle attachment in a holding position on or adjacent the dispenser outlet, with the nozzle supported stably in position adjacent to the outlet opening, but not opening the outlet closure valve. This may be practical e.g. when the coupling structure includes interfitting tubular portions of the outlet and nozzle attachment which slide or screw onto one another As mentioned, the idea is particularly useful with oral compositions such as oral medicines, for humans or animals. The volume of a pump chamber corresponding to a unit dosage can be determined accordingly, and for human use would usually be less than 20 ml, more usually not more than 10 ml, e.g. 10, 5 or 2.5 ml.

BRIEF DESCRIPTION OF THE DRAWINGS

These proposals are now illustrated by description of examples, with reference to the accompanying drawings in which.

DESCRIPTION OF THE SELECTED EMBODIMENTS

Figure 1:
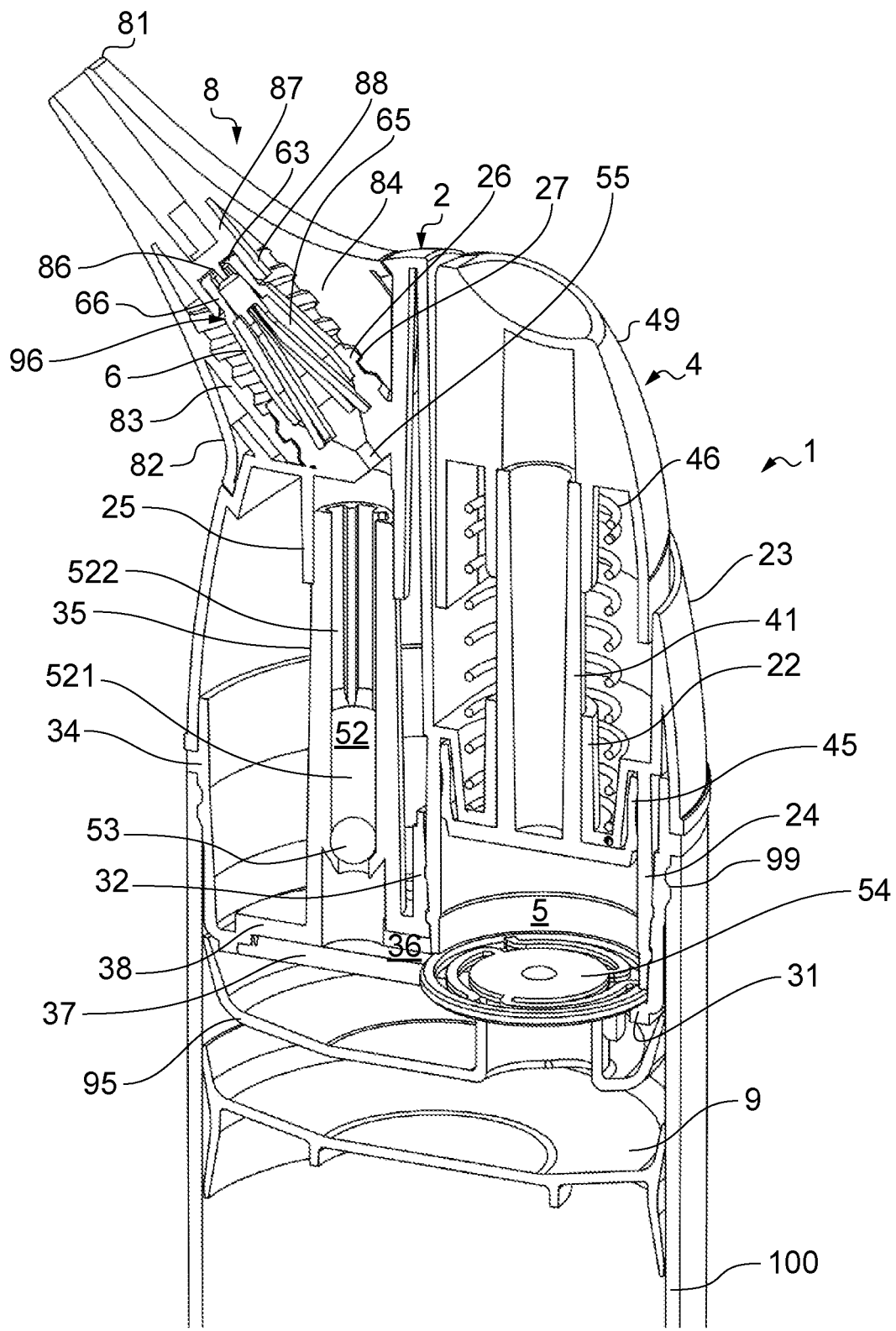
FIG. 1 is an axial cross-section though a fixed-nozzle dispenser.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 2:
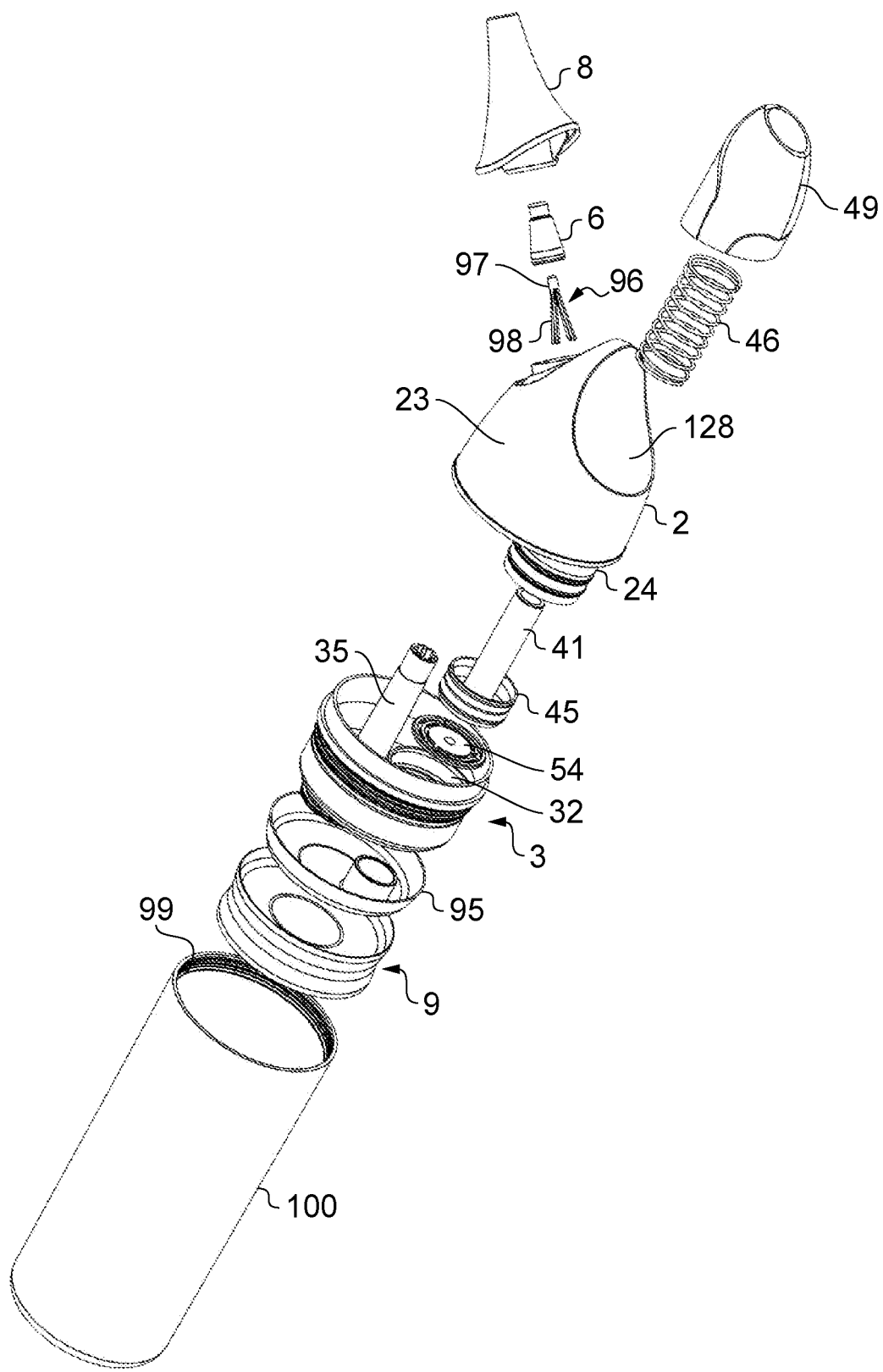
FIG. 2 is an exploded view of the FIG. 1 dispenser showing the main components.

Referring to FIGS. 1 and 2, a fixed-nozzle dispenser for dosing medicine to children comprises a product container 100 with snap ribs 99 around its top opening into which a pump unit 1 is fitted. A follower piston 9 is provided in the container 100 and rises as product is dispensed. The dispenser has a body mounting element 3 which plugs down into the container opening. The mounting element 3 is generally bowl-shaped, with an outer surround wall 34 which plugs into the container neck and a floor 38 with an eccentric inlet opening 31 controlled by an inlet valve 54. At a rear position, above the inlet opening 31, the mounting element 3 has an upwardly-extending socket 32 for a pump cylinder. At a front position an upward outlet tube 35 projects up from the floor 38 and houses an outlet ball valve 53. Above the conical valve seat the outlet tube 35 has an elongate bore 521 in which the valve ball 53 fits closely, and further up, a flow bore 522 with fins to guide the valve ball 53 separated by wall recesses to allow flow around it. In a dispensing stroke, the valve ball 53 rises until fluid can flow past it. After dispensing it falls and, once in the fitting bore 521, draws fluid back down away from the outlet structure.

A horizontal outlet channel 36 connects the vertical outlet passage 52 in the tube 35 with the pump chamber space 5 to the rear, and is closed off from beneath by a closure plate 37.

FIG. 1 also shows an air trap component 95 plugged into the underside of the base plate floor 38; this is as described in European Publication No. 2,353,727 published Aug. 10, 2011 and which is based on and claims priority to United Kingdom Application No. 1000601.0 which was filed on 14 Jan. 2010. This European publication is hereby incorporated by reference in its entirety. The European publication provides non-essential subject matter regarding the nozzle construction.

A top body element 2 fits down onto the body mounting element 3 to complete the pump flow system. The top body element 2 includes at the rear a pump cylinder 24 which plugs down into the cylinder socket 32 to define the pump chamber 5. At the front it has a downwardly-projecting socket 25 which connects down to the outlet tube 35 and leads up to a discharge outlet structure described in more detail below. The top body element 2 also has a surround shell 23 which fits down onto an upward collar of the mounting element 3 to enclose the flow control components. At the back of the pump this shell has a guide recess 128 in which a plunger button 49 of a pump plunger 4 is operable. This plunger button is on the top end of a piston stem 41 carrying a piston 45 at its bottom end. The piston 45 operates in the cylinder 24, the top wall of which projects inwardly connecting to an integrally-formed tubular stem guide 22. A return spring 46 between the button 49 and cylinder 24 urges the plunger button to the top position.

Figure 3:
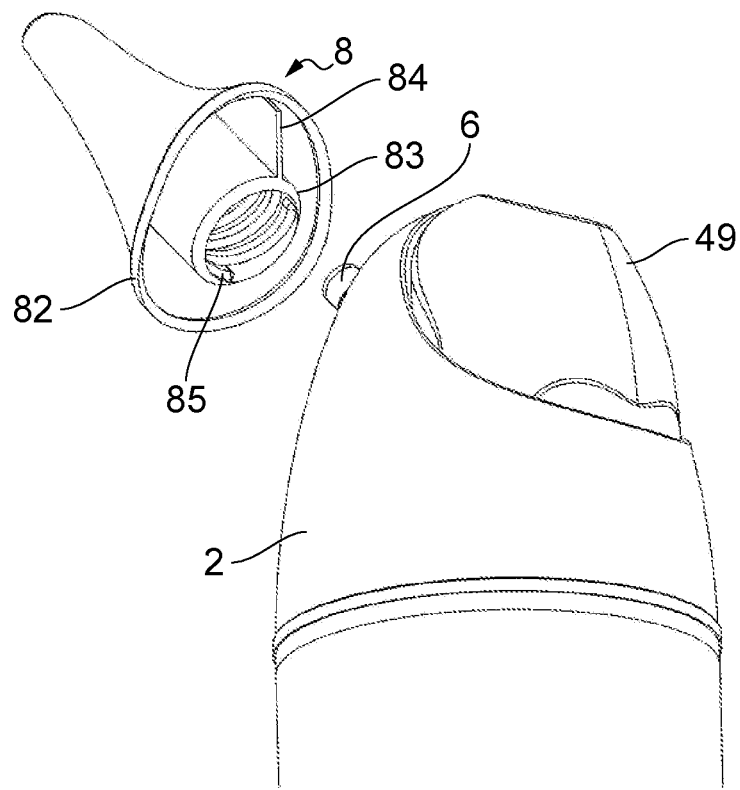
FIG. 3 and FIG. 4 are respectively rear and front oblique views showing a nozzle attachment in a detached condition.
Figure 4:
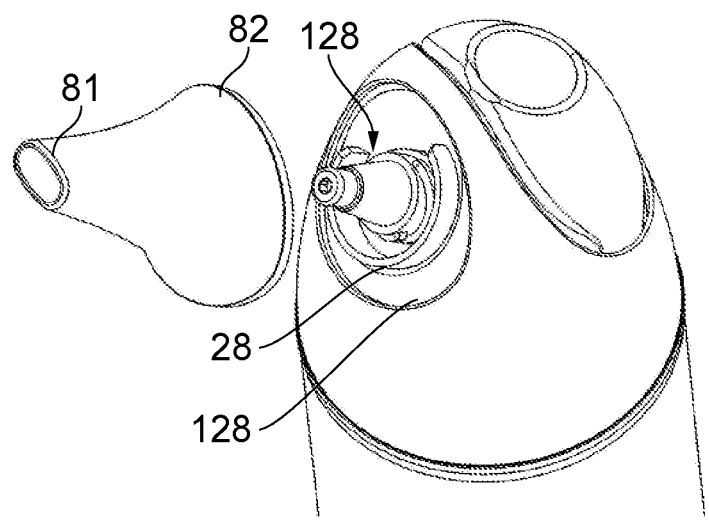
Figure 5:
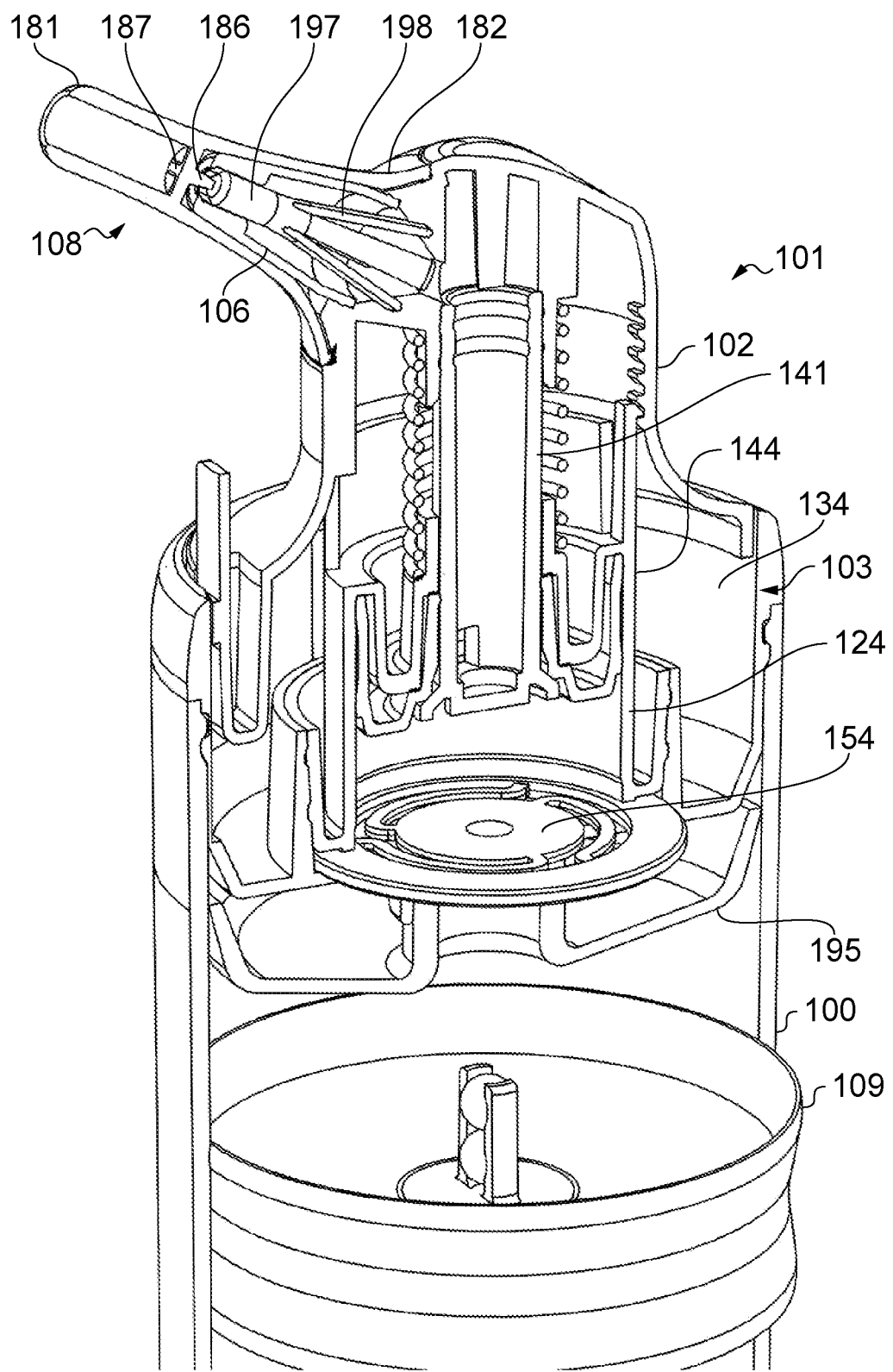
FIG. 5 is a second embodiment in a moveable-nozzle dispenser.
Figure 6:
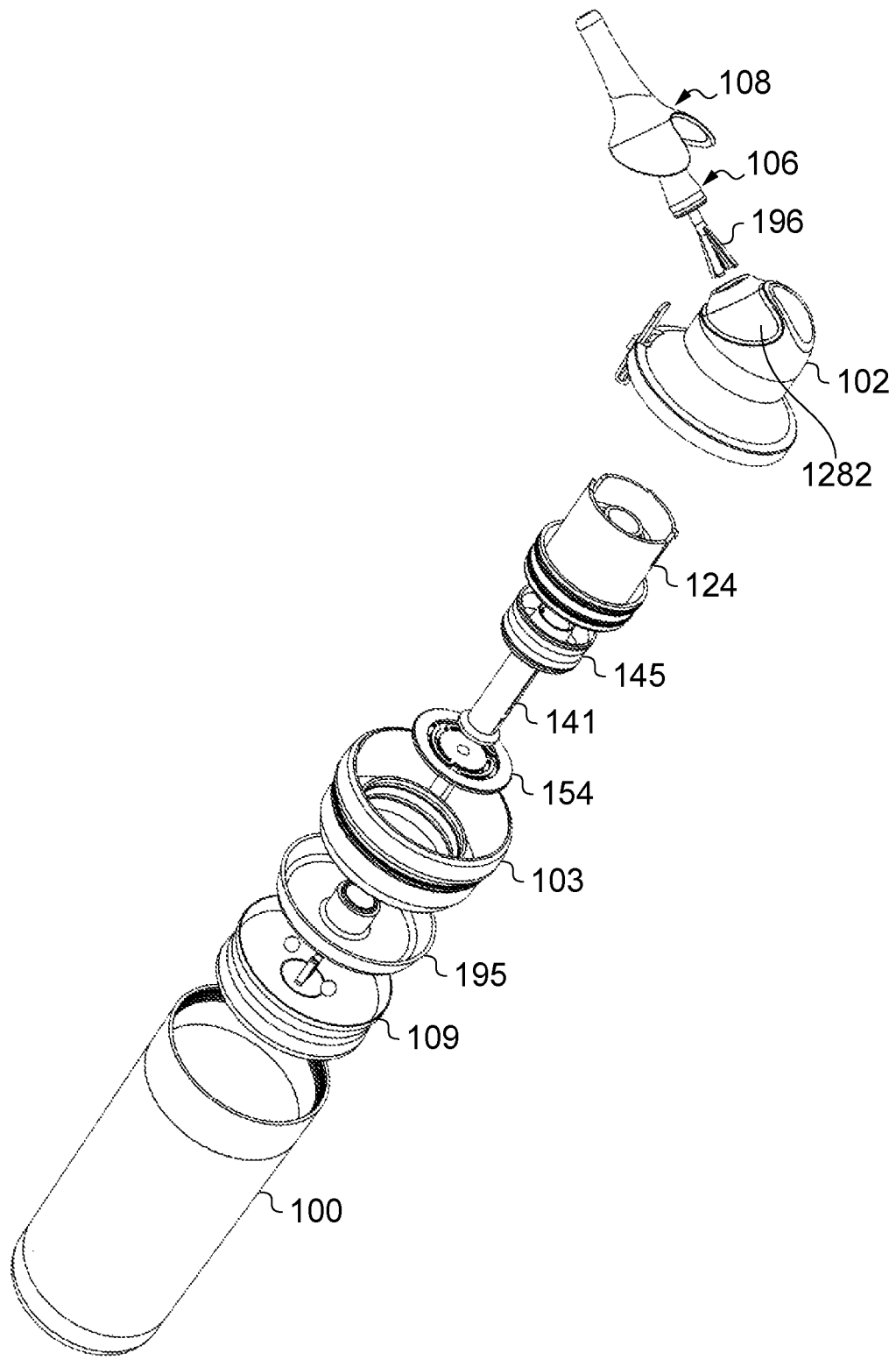
FIG. 6 is an exploded view of the FIG. 5 dispenser.

The characteristic outlet structure is described with reference to FIGS. 1, 3 and 4. The vertical outlet passage 52 communicates through top exit hole 55 to the exterior of body shell 2, emerging in the centre of a shaped socket recess 282 (see FIG. 4). It emerges through a stub mounting 26 with securing formations such as snap ribs or threads 27 on the outside, and smaller snap formations on the inside.

A stub nozzle 6 is plugged into the stub mounting 26. This is a conically-tapering tube with a tip discharge outlet opening 63 at the end of a parallel-sided tip flow section 66. Trapped in the cavity 65 inside the stub nozzle 6 is a one-piece closure valve element 96, with a front cylindrical plug fitting closely into the parallel-sided flow section 66 at the front of the stub nozzle, and a set of spring legs 98, formed integrally with the plug 97 as a single moulding, projecting back and seating in a conical depression around the flow exit opening 55 of the body shell 2. The parts are dimensioned to give slight pre-bending of the legs 98, so that the plug 97 is urged forwards to the outlet opening 63 where it fits closely in the plain circular opening and blocks all flow. Rearwardly of the opening the parallel-sided section has flow channels in its walls so that liquid can flow out past it when it is moved rearwardly, as seen in FIG. 1.

A removal nozzle attachment 8 fits over the stub nozzle 6. This attachment 8 is shaped with a flattened or beak-like front nozzle opening 81. It has a diverging outer skirt 82 which fits fittingly into the front recess 1282 of the body shell 2, merging smoothly with the exterior shape thereof, and an inner rear tube section 83 with an internal securing thread 85 which fixes onto the exterior securing formations 27 of the stub mounting 26. Half way along the inner tube 83—which leads through to the front nozzle 81—an inwardly-projecting open support structure 87 is formed integrally in the nozzle attachment 8. The support structure 87 carries a central rearwardly-projecting point 86 (actuating structure) which, with the nozzle 8 screwed in position, pushes the valve plug 97 back in the stub nozzle 6 against the spring of the legs 98 to allow outward flow. The central actuating structure includes a locating guide 88 which fits around the front end of the nozzle stub 6 to assure centring of the actuating point 86.

The shaped outer skirt 82 of the nozzle 8 allows a child can put as much or as little of the nozzle in their mouth as they wish, without meeting an uncomfortable boundary but without being able to push it too far in. The skirt 82 is continuous with the shape envelope of the top body shell 23 when in position, as shown in FIG. 1. Since this shell shape is not simple, the nozzle has only one correct alignment and this is assured by a ward structure comprising a barrier wall 28 with an open segment 1281 (see FIG. 4) on the front of the body shell 23 in the recess 1282 around the stub nozzle 6, co-operating with a radial fin 84 between the inner and outer parts of the nozzle 8 as seen in FIG. 3. The nozzle thread 85 can be engaged with the stub mounting 26 only when this ward fin is in the open clearance 1281, so that the right orientation (also with the longer dimension of the beak opening horizontal) is assured.

FIGS. 5 to 9 show a second embodiment with a modified form of nozzle attachment, this time in a moveable-nozzle dispenser unit 101 mounted on a container 100. Again a follower piston 109 is provided, and an air trap 195. As is conventional, the piston 144 and cylinder 124 of the pump are arranged centrally in the pump mounting member 103. The top cap shell is part of a plunger component, connecting to the piston stem 141 and piston 144 beneath; the piston stem and piston are discrete components with lost motion incorporating an outlet valve function as described in the United Kingdom application which is incorporated by reference by way of the European Publication. Components corresponding to those in the first embodiment are indicated by the same reference numerals plus 100.

Figure 7:
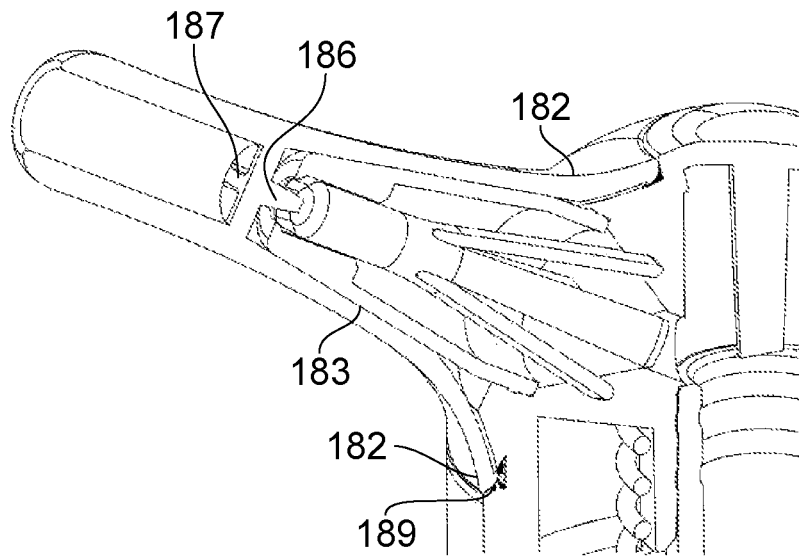
FIG. 7 shows the outlet structure with a nozzle attachment in place.
Figure 8:
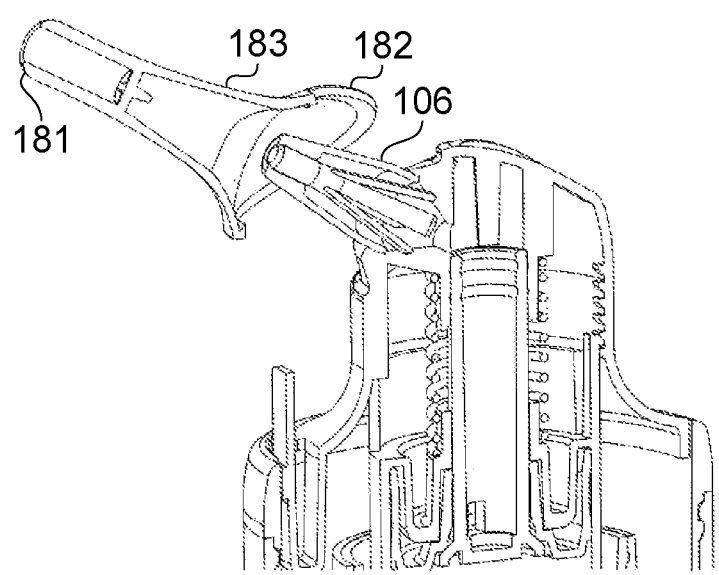
FIG. 8 shows the outlet structure with the nozzle attachment detached.
Figure 9:
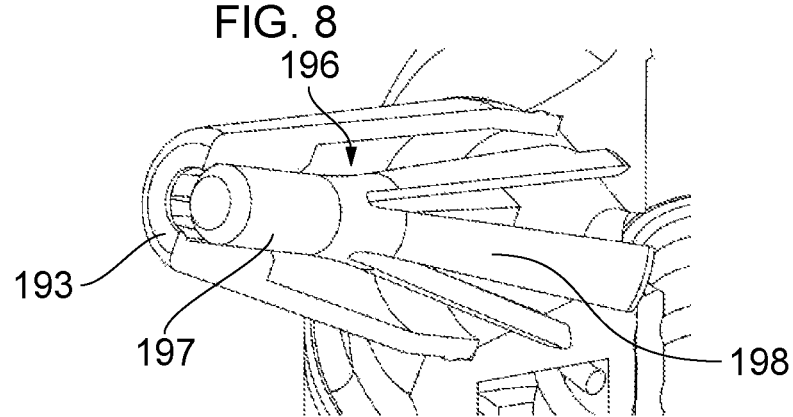
FIG. 9 shows detail of a closure valve mechanism, all of FIGS. 7 to 9 exposing the components by a vertical diametrical cross-section.

The nozzle attachment 108 has a simpler construction than that in the previous embodiment. Firstly its tip 181 is round rather than flattened. Secondly it does not have a distinct central tube locating at the base of the stub nozzle 106. Rather, it has a mid section 183 diverging so as to fit onto the outside of the stub nozzle 106 as seen in FIG. 7, the rearmost extension 182 again fitting into the shape envelope of a recess 1282 on the front face of the plunger shell 102 to provide a smooth contour. At the top and bottom of the skirt 182 there is a hooked engagement of a lip 189 (see FIG. 7) at the rim of the recess 1282 to make sure that the nozzle attachment 108 does not slide off.

The one-piece closure valve element 196 is essentially the same as in the first embodiment. The actuating structure in the nozzle 108 that pushes it open is rather simpler, consisting simply of a cruciform spoke array 187 formed integrally with the rearwardly-projecting actuating point 186.

With the nozzle removed, it will be seen that the outlet opening 63,163 is closed off essentially flush by the valve plug 97,197 and can easily be wiped or washed clean. The valve plug prevents product from being sucked from the dispenser when the nozzle is not fitted, and also isolates from the air any residual product in the discharge channel, preventing drying and contamination.

FIGS. 10 to 14 show a third embodiment, being a fixed-nozzle dispenser similar to the first embodiment but formed with a lower body profile and some variations of the detachable nozzle and its mounting. Generally the reference numerals correspond to those used in FIGS. 1 to 4 but with a 200 prefix.

Figure 10:
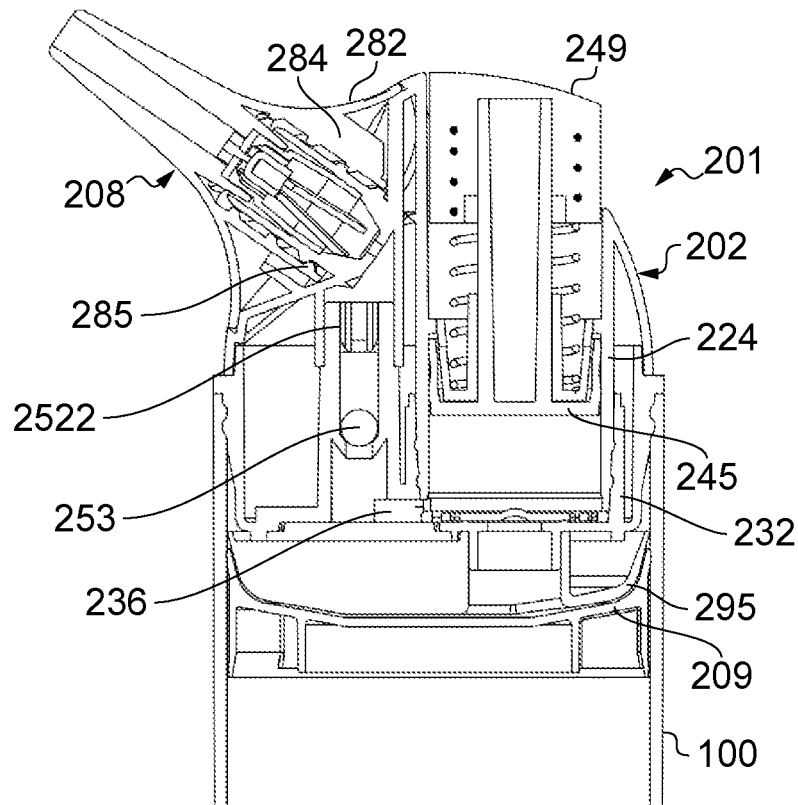
FIG. 10 is a vertical axial cross-section of a third embodiment of dispenser with a nozzle attachment fitted.
Figure 11:
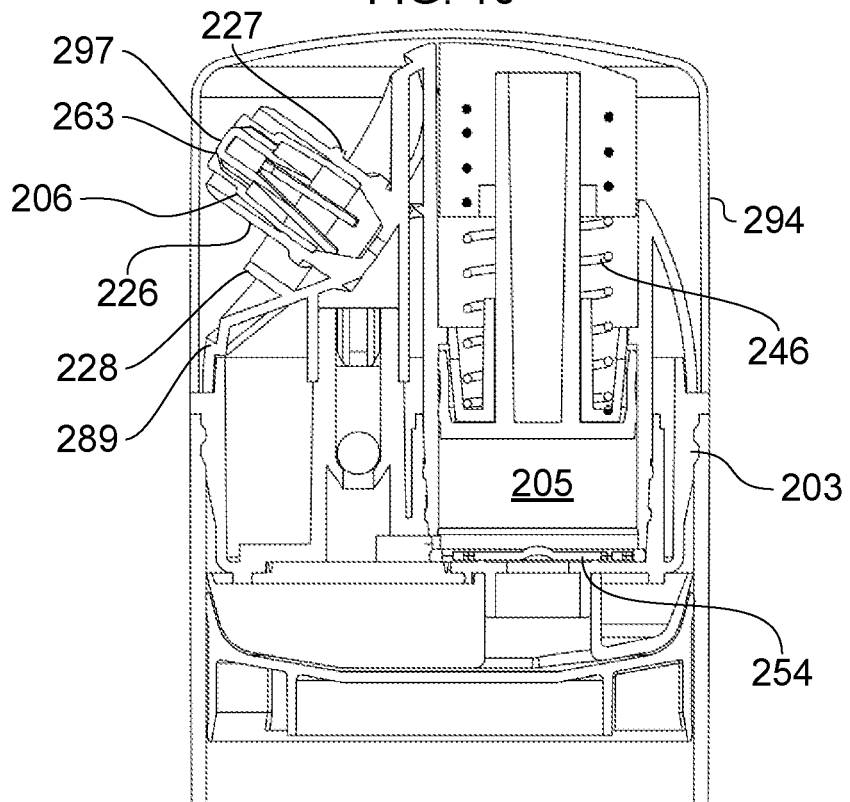
FIG. 11 shows the third embodiment with an outer cover cap fitted.

FIGS. 10 and 11 show a feature also used but not shown in the first and second embodiments, namely a generally cylindrical outer cover cap 294 (FIG. 11) which fits over the pump unit 201 when the nozzle attachment 208 has been removed, but not when it is in place.

The nozzle 208 has an outer skirt 282 and a rear union tube 283 with internal threads 285, substantially as in the first embodiment. A ward structure, with a guard wall 228 on the housing shell 202 having a clearance, and a corresponding fin 284 on the nozzle 208, ensures that the nozzle can be applied only in the correct orientation.

Here the nozzle tip opening 281 is round, so orientation is needed to merge the nozzle skirt 282 properly into the shape of the body shell 202. It also enables a further child-resistant feature described below.

The nozzle stub 206 plugs into a stub housing/nozzle mounting socket 226 which in this example is formed longer, extending out to about the same length as the nozzle stub 206, with a small annular clearance between them. As before, the outside of the stub housing 206 carries mounting threads 227 to engage the interior threads 285 of the rear nozzle tube 283.

Figure 14:
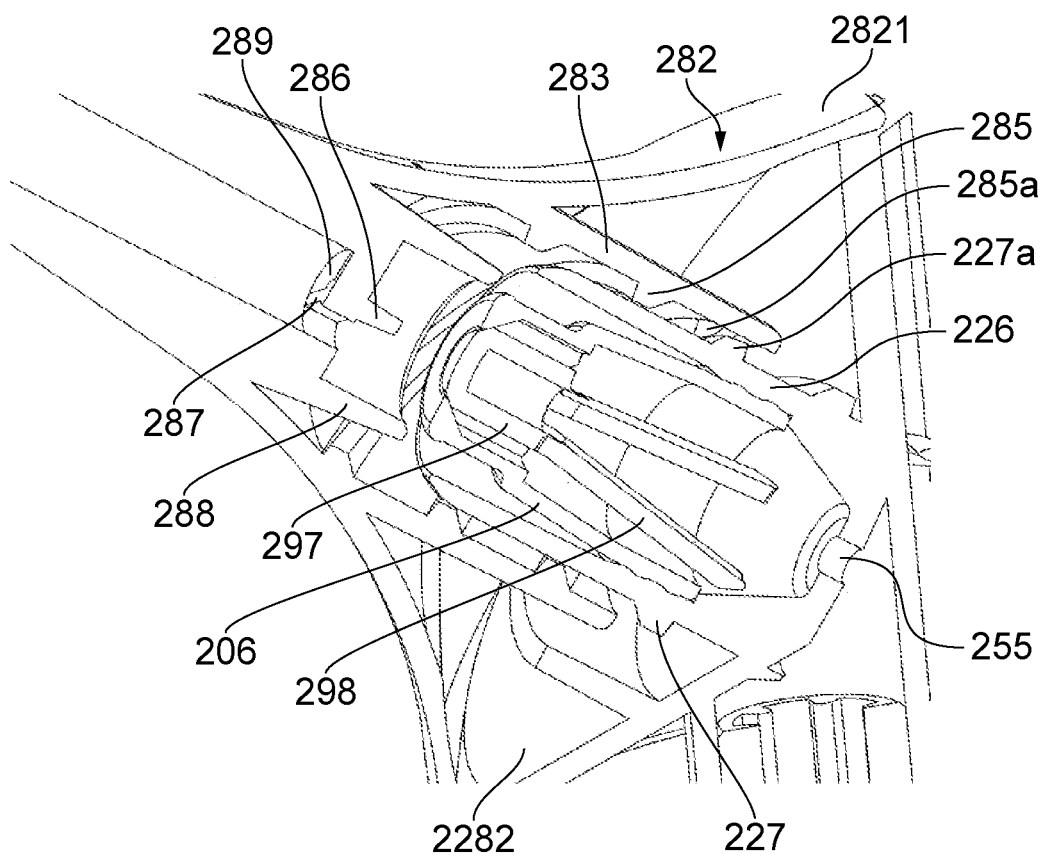
FIG. 14 is a fragmentary medial section through the nozzle attachment and stub nozzle in the FIG. 13 position.

As before, the interior of the nozzle carries closure-actuating structure, namely a rearwardly-projecting central member 286 supported by a spoked support structure 287. Openings 289 between the spokes are shown in FIG. 14. A tubular surround guide 288 fits around the tip of the stub nozzle 206, entering the annular clearance between this and the surrounding stub mounting 226. The internal valve 297,298 is substantially as in the first embodiment.

Figure 12:
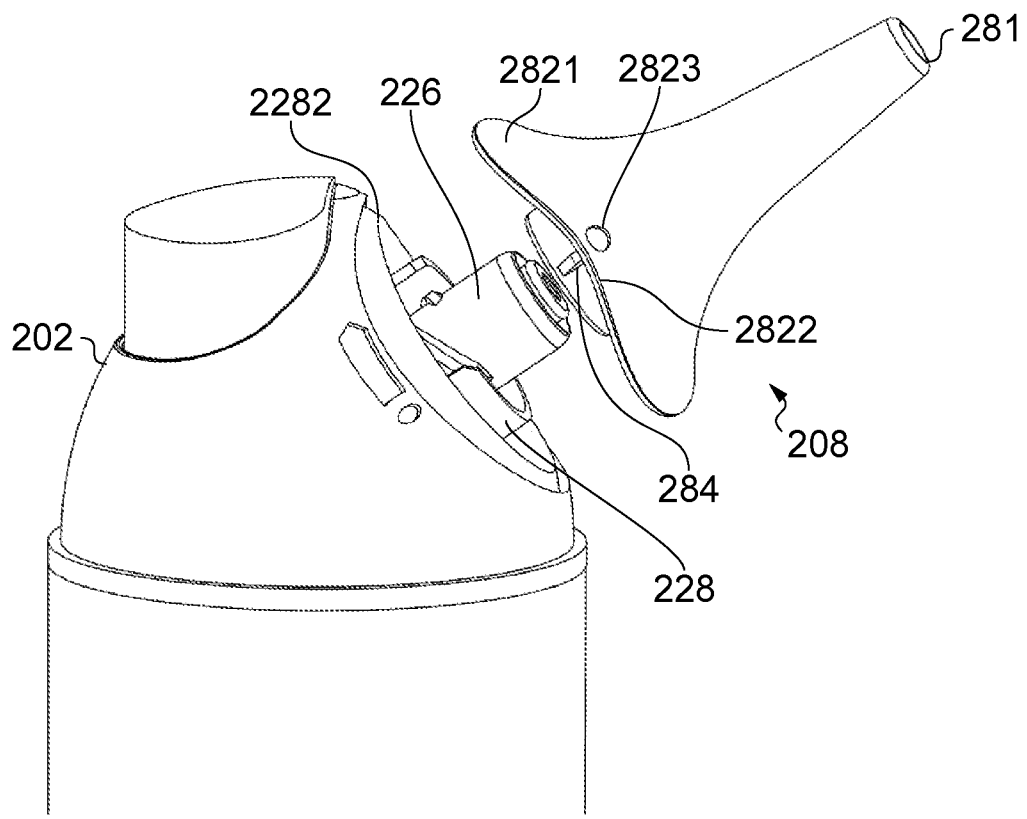
FIGS. 12 and 13 show stages of fitting the nozzle attachment.
Figure 13:
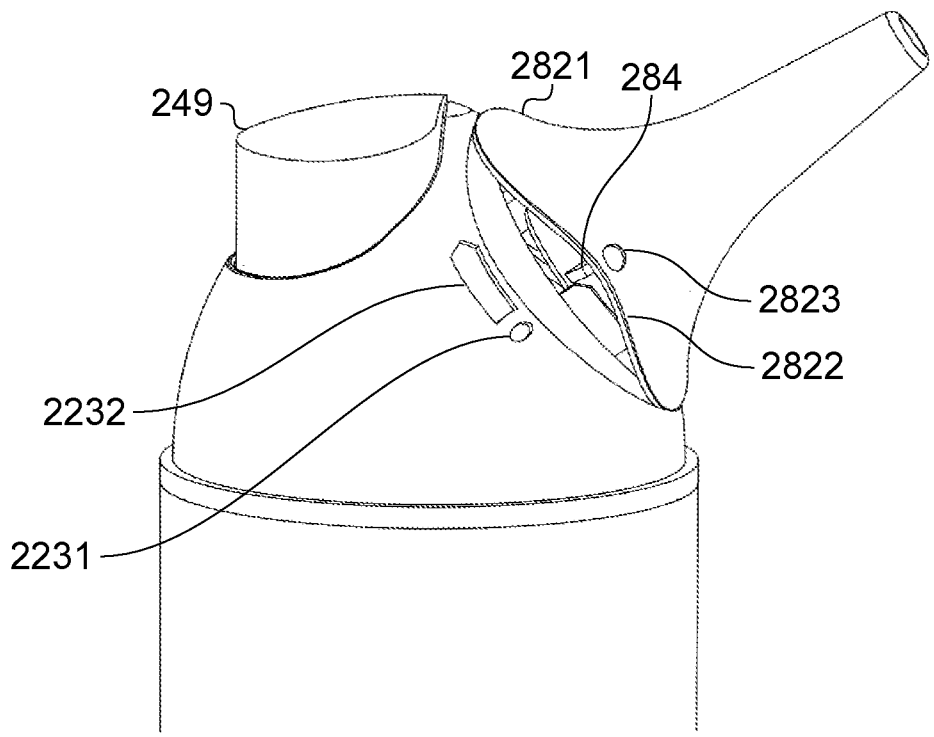

FIGS. 12 and 13 show that the skirt 282 of the nozzle 208 has a pair of diametrically-opposed lobes 2821 with relatively recessed portions 2822 between. To be screwed on, the nozzle must be presented to the mounting 226 with its ward fin 284 aligned with the clearance in the ward wall 228 on the body. This alignment is indicated to the user by a visual marker 2823 on the nozzle skirt edge, to be lined up with a corresponding marker 2231 on the body shell next to the edge of the recess 2282 which receives the nozzle skirt. From here, a quarter-turn of the thread is enough to lock and seal the nozzle in position. However as presented, the lobes 2821 of the skirt 282 meet the top and bottom of the body recess 2282 before the threads can engage. FIG. 14 shows the nozzle thread start 285*a* not reaching behind the stub mounting thread start 227*a*. In this position clockwise turning of the nozzle (e.g. by a child imitating an adult) does not engage the threads, secure the nozzle or open the valve closure member 297 of the stub nozzle 206. It is necessary first to push on the nozzle, bending the skirt lobes 2821 so that the thread starts 227*a*,285*a* can engage. A further arrow marker 2232 on the body shell 202 (FIG. 13) shows the user which way to turn the nozzle. Thus, the construction has a first level of child resistance in that the nozzle cannot be attached unless the markers are lined up, and a second level of child resistance in that the nozzle then cannot be attached and opened for use unless both pushed and turned at the same time.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A dispenser for a fluid product, comprising
a dispenser body, a supply container and an outlet attachment;
the dispenser body having a discharge outlet and the dispenser being operable to dispense a fluid product from the supply container in doses from said discharge outlet, wherein the discharge outlet has an outlet closure valve with a closure mechanism including a closure member which in a closed position closes the discharge outlet;
the outlet attachment defining an outlet conduit having a nozzle opening;
the dispenser body and the outlet attachment including coupling structure whereby the outlet attachment can be coupled to the dispenser at the discharge outlet; and
the outlet attachment further including an actuating structure which in a coupled condition, with the outlet attachment coupled to the dispenser at the discharge outlet, engages the closure mechanism of said outlet closure valve to hold the closure valve in an open condition, thereby putting the dispenser discharge outlet in fluid communication with the outlet conduit and nozzle opening of the outlet attachment so that fluid product can be dispensed from the dispenser through the outlet attachment.

2. The dispenser according to claim 1 in which the closure member of the outlet closure valve is spring biased so as automatically to close the discharge outlet when the outlet attachment is uncoupled.

3. The dispenser according to claim 2 in which the outlet closure valve is arranged so as to be urged to the closed position by fluid pressure in the dispensing direction in the dispenser discharge outlet.

4. The dispenser according to claim 1 in which the closure member of the outlet closure valve is at the outlet opening of the discharge outlet in the closed position.

5. The dispenser according to claim 1 in which the dispenser body has a projecting outlet stub defining said discharge outlet, the outlet attachment fitting onto the outlet stub in the coupled condition.

6. The dispenser according to claim 1 in which said outlet attachment is a generally tubular component including a socket or plug portion shaped to fit onto a corresponding formation at the outlet opening of the dispenser, and said outlet attachment comprises said actuating structure in the form of a rearwardly-directed projection.

7. The dispenser according to claim 6 in which said actuating structure is mounted inside the tubular outlet attachment by support structure comprising one or more support elements or spokes.

8. The dispenser according to claim 1 which is a pump dispenser, comprising a pump unit with a pump plunger reciprocable to alter the volume of a pump chamber which is defined in the pump unit and is connected via a valved inlet to the supply container and via a discharge channel to the dispenser discharge outlet.

9. The dispenser according to claim 8 in which the pump chamber is defined between a piston and cylinder, the piston moving with the pump plunger.

10. The dispenser according to claim 8 in which the volume of the pump chamber, corresponding to a unit dose, is up to 5 ml.

11. The dispenser according to claim 8 in which the pump dispenser unit is a fixed-nozzle dispenser, the discharge channel and outlet opening thereof being a part of or fixed relative to a pump body which secures to the supply container.

12. The dispenser according to claim 1 in which the outlet attachment has, around behind its nozzle opening, a smoothly curved tapering external surround surface for putting in the mouth.

13. The dispenser according to claim 1 in which
the closure member of the outlet closure valve is at the outlet opening of the discharge outlet in the closed position and is spring biased so as automatically to close the discharge outlet when the outlet attachment is uncoupled;
the dispenser body has a projecting outlet stub defining said discharge outlet, the outlet attachment fitting onto the outlet stub in the coupled condition; and
said outlet attachment is a generally tubular component including a socket or plug portion shaped to fit onto a corresponding formation at the outlet opening of the dispenser, and said outlet attachment comprises said actuating structure in the form of a rearwardly-directed projection to engage and push back said closure member in the coupled condition.

14. The dispenser according to claim 13 in which said actuating structure is mounted inside the tubular outlet attachment by support structure comprising one or more support elements or spokes.

15. The dispenser according to claim 13 which is a pump dispenser, comprising a pump unit with a pump plunger reciprocable to alter the volume of a pump chamber which is defined in the pump unit.

16. A dispenser for fluid product, comprising:
a dispenser body, the dispenser body having a discharge outlet and the dispenser being operable to dispense a fluid product from a fluid supply in doses from said discharge outlet;
said discharge outlet defining an outlet opening and including an outlet closure valve and a closure mechanism including a closure member which is biased towards a closed position in which it closes the discharge outlet at the outlet opening to prevent dispensing of fluid product under forward fluid pressure;
the dispenser body including a projecting outlet stub, the outlet stub including the discharge outlet and constituting a coupling structure for the removable coupling of a removable tubular nozzle attachment onto the discharge outlet; and
whereby in a coupled condition, in which said nozzle attachment is coupled to the outlet stub, and in which an actuating structure of the nozzle attachment engages the closure mechanism of said outlet closure valve to hold said outlet closure valve in an open condition, the dispenser discharge outlet is in fluid communication with the nozzle attachment so that fluid product can be dispensed from the dispenser through the outlet attachment, whereas in an uncoupled condition or absence of such nozzle attachment, dispensing of fluid product under forward fluid pressure is prevented by said outlet closure valve.

17. The dispenser according to claim 16 further comprising a said removable nozzle attachment which comprises a socket or plug portion shaped to fit onto the outlet stub of the dispenser, and also comprises said actuating structure in the form of a rearwardly-directed projection to engage and push back the closure member of the outlet closure valve against said bias thereof in the coupled condition.

18. The dispenser according to claim 17 in which said removable nozzle attachment has a smoothly curved forwardly-tapering external surround surface.

19. The dispenser according to claim 16 which is a fixed-nozzle pump dispenser, comprising a pump unit with a pump plunger reciprocable to alter the volume of a pump chamber which is defined in the pump unit and is connected via a valved inlet to the supply container and via a discharge channel to the dispenser discharge outlet, the pump chamber being defined between a piston and cylinder, the piston moving with the pump plunger, and the discharge channel and outlet opening thereof being fixed relative to a pump body which secures to a fluid product supply container of the dispenser.

20. The dispenser according to claim 19 in which the volume of the pump chamber, corresponding to a unit dose, is up to 5 ml.

21. In combination:
a supply container;
a dispenser body assembled to said supply container, said dispenser body having a discharge outlet with a normally-closed outlet closure valve including a closure member; and
an outlet attachment assembled to the dispenser body adjacent the discharge outlet, said outlet attachment including an outlet and an actuating structure which is constructed and arranged to move said closure member to open said outlet closure valve for dispensing, when the outlet attachment is assembled to the dispenser body.

22. The combination of claim 21 wherein said closure member includes a plug portion and said actuating structure engages said plug portion for movement of said closure member.

23. The combination of claim 21 wherein said discharge outlet is defined by a nozzle and said outlet attachment fits over said nozzle.

24. In combination:
a supply container;
a dispenser body assembled to said supply container, said dispenser body having a discharge outlet with a normally-closed outlet closure valve including a closure member; and an outlet attachment assembled to the dispenser body adjacent the discharge outlet, said outlet attachment including an actuating structure which is constructed and arranged to move said closure member to open said outlet closure valve, wherein said closure member includes a plug portion and said actuating structure engages said plug portion for movement of said closure member.

25. The combination of claim 21 wherein the closure member of the outlet closure valve is spring biased so as to close the discharge outlet when the outlet attachment is disassembled from the dispenser body.

26. The combination of claim 25 wherein the outlet closure valve is constructed and arranged so as to be urged to a closed position by fluid pressure in a dispensing direction in the discharge outlet.

27. The combination of claim 26 wherein the closure member is at an outlet opening of the discharge outlet in a closed position.

28. The combination of claim 21 wherein the outlet closure valve is constructed and arranged so as to be urged to a closed position by fluid pressure in a dispensing direction in the discharge outlet.

29. The combination of claim 24 wherein said discharge outlet is defined by a nozzle and said outlet attachment fits over said nozzle.

30. The combination of claim 24 wherein the closure member of the outlet closure valve is spring biased so as to close the discharge outlet when the outlet attachment is disassembled from the dispenser body.

31. The combination of claim 30 wherein the outlet closure valve is constructed and arranged so as to be urged to a closed position by fluid pressure in a dispensing direction in the discharge outlet.

32. The combination of claim 31 wherein the closure member is at an outlet opening of the discharge outlet in a closed position.

* * * * *